(12) United States Patent
Hruschka et al.

(10) Patent No.: US 10,092,021 B2
(45) Date of Patent: *Oct. 9, 2018

(54) METHOD FOR OBTAINING VALUABLE PRODUCTS, IN PARTICULAR PROTEINS, FROM A NATIVE MIXTURE OF MATERIALS

(71) Applicant: GEA Mechanical Equipment GmbH, Oelde (DE)

(72) Inventors: Steffen Hruschka, Oelde (DE); Wladislawa Boszulak, Oelde (DE); Detlef Ullmann, Oelde (DE); Juergen Rassenhoevel, Oelde (DE)

(73) Assignee: GEA Mechanical Equipment GmbH, Oelde (DE)

( * ) Notice: Subject to any disclaimer, the term of this patent is extended or adjusted under 35 U.S.C. 154(b) by 497 days.

This patent is subject to a terminal disclaimer.

(21) Appl. No.: 14/758,147

(22) PCT Filed: Dec. 20, 2013

(86) PCT No.: PCT/EP2013/077621
§ 371 (c)(1),
(2) Date: Jun. 26, 2015

(87) PCT Pub. No.: WO2014/102176
PCT Pub. Date: Jul. 3, 2014

(65) Prior Publication Data
US 2015/0327572 A1    Nov. 19, 2015

(30) Foreign Application Priority Data

Dec. 27, 2012  (DE) .......................... 10 2012 113 100
Apr. 18, 2013  (DE) .......................... 10 2013 103 910

(51) Int. Cl.
*A61K 36/48*    (2006.01)
*A23J 1/00*    (2006.01)
(Continued)

(52) U.S. Cl.
CPC ............... *A23J 1/006* (2013.01); *A23J 1/142* (2013.01); *C07K 1/36* (2013.01)

(58) Field of Classification Search
CPC ...................................................... A61K 36/48
(Continued)

(56) References Cited

U.S. PATENT DOCUMENTS 2,667,973 A    2/1954 Lindgren
3,876,806 A *  4/1975 Hempenius ............. A23J 3/346
                                                          426/18
(Continued)

FOREIGN PATENT DOCUMENTS

DE           195 29 795 C2    2/1996
DE      10 2011 050 905 A1   12/2012
(Continued)

OTHER PUBLICATIONS

PCT/EP2013/077621, International Search Report (PCT/ISA/220 and PCT/ISA/210) dated May 23, 2014, with partial English translation, enclosing Written Opinion of the International Searching Authority (PCT/ISA/237) (Thirteen (13) pages).
(Continued)

*Primary Examiner* — Christopher R Tate
(74) *Attorney, Agent, or Firm* — Crowell & Moring LLP

(57) ABSTRACT

A method for obtaining proteins from native mixtures of materials is disclosed. In an embodiment, the method includes: A): providing a native mixture of materials from seeds having hard fragmentable hulls; B): comminuting the mixture of materials; C): dispersing the comminuted mixture of materials with water; D): adjusting a pH of the pulp of step C) to an alkaline range pH>9.5; E): adding a water-soluble organic solvent alcohol to the pulp; F): separating off a solids phase from the pulp, which has a predominant fraction of the hulls, to form a hull-free pulp; G): shifting the
(Continued)

Step S6) Separation 1

Separation stage 1: Separation of hull from residual pulp (containing protein, PP, carbohydrate, oil, lecithin)

pH of the hull-free pulp from step F) to a pH range of pH=4.5 to pH=7.2; and H): separating the hull-free pulp of step G) into a plurality of phases, wherein one of the plurality of phases is a protein concentrate phase.

24 Claims, 4 Drawing Sheets

(51) Int. Cl.
 *C07K 1/36* (2006.01)
 *A23J 1/14* (2006.01)
(58) Field of Classification Search
 USPC .............................. 424/725, 757, 768, 776
 See application file for complete search history.

(56) References Cited

U.S. PATENT DOCUMENTS

| | | | | |
|---|---|---|---|---|
| 4,077,950 | A | * | 3/1978 | White .................. A23J 1/006 530/370 |
| 4,409,256 | A | * | 10/1983 | Johnson ................ A23L 11/31 426/471 |
| 2004/0042996 | A1 | * | 3/2004 | Pauly .................... A61K 8/645 424/74 |
| 2006/0193930 | A1 | * | 8/2006 | Rao ......................... C07K 2/00 424/757 |
| 2014/0057030 | A1 | * | 2/2014 | Kirchner ............... C10G 1/047 426/416 |
| 2014/0228550 | A1 | * | 8/2014 | Hruschka ............... A23J 1/006 530/422 |

FOREIGN PATENT DOCUMENTS

| | | |
|---|---|---|
| GB | 842356 | 7/1960 |
| RU | 2 218 816 C2 | 12/2003 |
| WO | WO 01/76385 A1 | 10/2001 |
| WO | WO 03/053157 A1 | 7/2003 |

OTHER PUBLICATIONS

German Search Report dated Dec. 11, 2013, with Statement of Relevancy (Six (6) pages).
Kroll et al., "Rapssamenproteine—Struktur, Eigenschaften, Gewinnung und Modifizierung" [Rapeseed proteins—Structure, properties production and modification], Deutsche Lebensmittel-Rundschau, No. 3, 2007, pp. 109-119.
Makkar et al., "Protein concentrate from Jatropha curcas screw-pressed seed cake and toxic and antinutritional factors in protein concentrate", Journal of the Science of Food and Agriculture, 88, 2008, pp. 1542-1548.—ISSN 0022-5142.
Menner et al., "Fraktionierung pflanzlicher Rohstoffe zur simultanen Erzeugung von Lebensmitteln, technischen Rohstoffen und Energietraegern" [Fractionation of plant raw materials for simultaneous generation of foods, industrial raw materials and energy carriers], Chemie Ingenieur Technik, vol. 81, issue 11, pp. 1743-1756, Nov. 2009.
Tan et al., "Canola Proteins for Human Consumption: Extraction, Profile, and Functional Properties", Journal of Food Science, 76, 2011, pp. R16-R28.—ISSN 1750-3841.
U.S. Appl. No. 14/124,561, "Process for Obtaining Proteins from a Native Substance Mixture", filed Jun. 6, 2012, Inventor Steffen Hruschka, et al.
Russian-language Search Report issued in counterpart Russian Application No. 2015013030 dated Sep. 14, 2017 (Two (2) pages).

\* cited by examiner

METHOD FOR OBTAINING VALUABLE PRODUCTS, IN PARTICULAR PROTEINS, FROM A NATIVE MIXTURE OF MATERIALS

This application claims the priority of International Application No. PCT/EP2013/077621, filed Dec. 20, 2013, and German Patent Document Nos. 10 2012 113 100.7, filed Dec. 27, 2012, and 10 2013 103 910.3, filed Apr. 18, 2013, the disclosures of which are expressly incorporated by reference herein.

BACKGROUND AND SUMMARY OF THE INVENTION

The present invention relates to a method for obtaining valuable products, in particular proteins, from a native mixture of materials.

In this case, using the present invention, a processing as extensive as possible of this mixture of materials is to proceed to obtain valuable products.

DE 195 29 795 C2 discloses a method which permits oils or fats to be obtained. In this method, an aqueous pulp is separated in a centrifuge into solid and liquid components. To the aqueous pulp is added a fraction of 5-75% by weight, based on the liquid fraction of the pulp, of an organic solvent. DE 195 29 795 C2 here addresses the problem of isolating a clear oil phase, a water phase, and a solids phase freed from oil from the aqueous pulp. This method has proved fundamentally successful for obtaining oils, waxes and fats.

Known methods for protein production are protein isolate production at an alkaline pH, or protein concentrate production at an acidic pH, which are preferably used in the case of hexane-extracted meal, but which, in combination with the method of DE 195 29 795 C2 are not applicable to a protein-lecithin mixture without a prior energy-intensive drying step.

In the literature, further publications for producing protein products from deoiled raw materials are cited, for instance Kroll et al., "Rapssamenproteine—Struktur, Eigenschaften, Gewinnung und Modifizierung" [Rapeseed proteins—Structure, properties production and modification], Deutsche Lebensmittel-Rundschau, number 3, 2007, p. 109.

These methods generally proceed from deoiled raw materials. Typical test oil contents are 1-4%. Should this not be the case, solvent extractions are performed, in order to reduce the oil value to an unavoidable minimum. These raw materials must therefore be deoiled because the oil interferes many times in the familiar methods. It always remains in the anhydrous phase, and is therefore part of the dry matter. Therefore, it remains in the protein cake or protein concentrate, that is to say as an impurity of the protein.

Some methods also use filter techniques. The filters can become blocked with the oil fraction which is present in emulsified form. Protein losses in the protein isolate are associated therewith.

This is the established approach to protein concentrate production: washing the meals (intensively deoiled), wherein the soluble extracted materials are depleted. The value of the deoiled intermediate products depends greatly on the concentration of accompanying materials, such as fibers, sugars and secondary plant materials (Menner, M. et al. "Fraktionierung pflanzlicher Rohstoffe zur simultanen Erzeugung von Lebensmitteln, technischen Rohstoffen und Energietragern" [Fractionation of plant raw materials for simultaneous generation of foods, industrial raw materials and energy carriers], Chemie Ingenieur Technik, volume 81, issue 11, pages 1743-1756, November 2009).

These accompanying materials also include polyphenols such as sinapine. In order to separate off these materials, high dilutions are selected, also proteins are denatured (temperature, alcohol), cellulose is enzymatically degraded to form short-chain carbohydrates; these methods are selected in order to be able to extract the materials better.

Protein concentrates remain behind, the protein fraction of which is increased if, in advance, hulling was performed which reduces the hull fraction and/or the cellulose fraction.

All of the methods have in common the fact that soluble proteins (albumins, some globulins) are co-extracted together with the polyphenols, carbohydrates and other dissolved materials.

Other approaches proceed from a very fine comminution, but then, also, the cellulosic hull fragments have to be separated off from the protein. The smaller they are, the more difficult the classification is and the separation of the material in general. The protein concentrate phase remains contaminated. Thus, a mechanical comminution of the meal/cake or an intense shearing of the meal or cake dispersion, optionally further associated with an enzymatic treatment, always leads to smaller cellulose units down to short-chain carbohydrates. In the attachment (FIGS. 4a, b), it may be seen, by way of example, that a broken cake has a maximum in the granulometric distribution at about 600 µm, and only a little-expressed relative maximum at 8-10 µm.

By shearing, the volume fraction of the global maximum at approximately 600 µm is disadvantageously reduced from approximately 5.5% to approximately 4.5%, and in consequence thereof, the relative maximum of the small particles at approximately 8 increases to above 1%. The protein phase is grayer as a result.

These small particles are difficult to separate from the protein. Extraction remains as a method, in high dilutions or multi-stage.

DE 10 2011 050 905 A1 additionally discloses a method for obtaining proteins from native mixtures of materials in which a native mixture of materials is first finely comminuted and optionally, by addition of a liquid, processed to form a free-flowing pulp. The method in addition has the following steps: adjusting the pH of the pulp to an alkaline range; addition of at least one water-soluble organic solvent subsequently to the adjustment of the pH of the pulp; and separating off a protein phase from the pulp subsequently to the addition of the water-soluble solvent. In addition, separating off a solids phase having a hull fraction from the pulp before this phase separation is disclosed. Maintaining the sequence of these steps is particularly advantageous. In this case, in contrast to that in DE 195 29 795 C2, before the addition of the water-soluble organic solvent, a pulp pH is adjusted to an alkaline range. As a result, the solubility of the proteins in the aqueous medium is increased, they are partially solubilized and, if they are not completely dissolved, at least present finely distributed and voluminous in the solution and not in compact form as are the remaining solids. A complete solubility of the proteins is interfered with by the presence of a protein-lecithin mixture. Subsequently to the adjustment of the pH, the organic water-soluble solvent is added, as a result of which, inter alia, oil, in particular the triglycerides and nonpolar materials, are displaced from the solubilized protein suspension.

The method of DE 10 2011 050 905 A1 thus permits proteins of high purity to be obtained, since, inter alia, owing to the increase in solubility of the proteins, bonds, for example to contaminants of cellulose and/or hulls, and the like are also apparently loosened.

Usually, the first step is a pressing operation for deoiling or partial deoiling. In this case the hulls form a framework in order to form a press cake. Even in the case of hulled seed, a necessary minimum of hulls remains for the pressing.

Owing to the pressing operation, adherence of the proteins to the hulls occurs. In this case, the higher the pressing pressure or the temperature are, the firmer the cotyledon adheres to the hulls and the more difficult it is to separate it off later from the hulls to obtain protein. Protein losses are caused thereby.

Against this background, nevertheless, the object of the invention remains, optimizing further the obtaining of valuable materials from the native mixture of materials.

Hereinafter, an advantageous method variant of the invention will be explained in more detail, wherein the drawings will also be utilized.

DETAILED DESCRIPTION OF THE DRAWINGS

Figure 1:
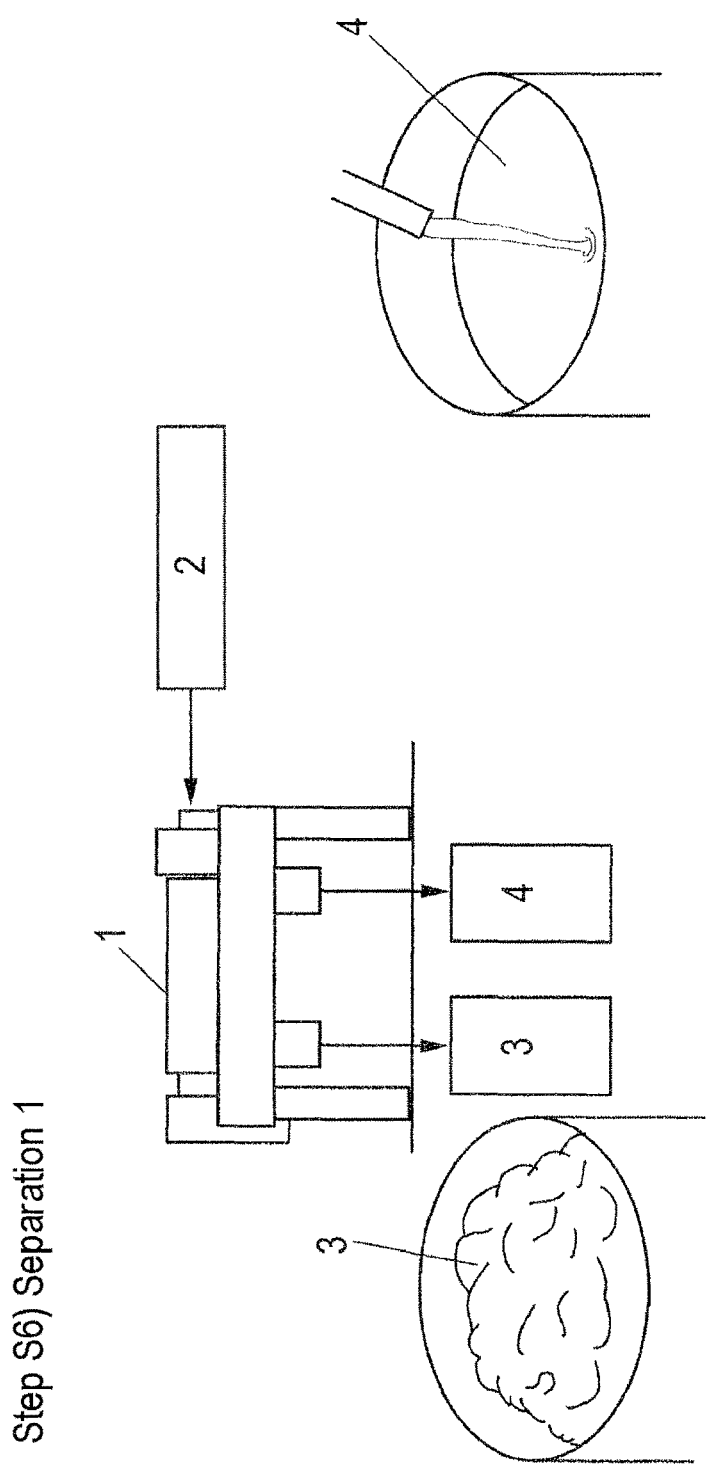
FIG. 1 shows a decanter 1 having a feed 2, wherein the hulls 3 are separated from the residual pulp 4.

The method according to the invention preferably has the following steps:

Step A:

The starting material provided is native mixture of materials from seeds having hard fragmented hulls, in particular
  whole legume seeds/fruits,
  whole sunflower seeds (seeds or fruits of *Helianthus annuus*) or soybeans, and/or
  whole seeds/fruits of Brassicaceae, in particular of rape fruits.

The mixture of materials in the context of this application can consist of the whole, but broken, seeds.

Alternatively, the mixture of materials can also consist of a previously deoiled product, in particular of an "intermediate product", that is to say of a press cake, which remains as a residue of oil extraction after a "preliminary stage", e.g. the pressing out of oil, in particular using a press (e.g. a screw press).

Particularly preferably, the starting material processed is "intermediate product obtained shortly before", that is to say after the preliminary stage, no more than 31 days shall have passed.

The seed can be freshly harvested, or else be days, weeks or months old, the intermediate stage (the pressing) should take place shortly before, or even directly before, the further processing, in order that, after the oil extraction, the material—the seed—has not changed too greatly.

Very preferably, the starting material processed is "fresh material", that is to say, after a preliminary stage, or a preliminary processing (oil extraction), no more than 3 days shall have passed, and preferably even fewer than 48 hours, or 24 hours, or 12 h, or less than 1 h.

Using materials from a period shortly after the preliminary stage, good results, or and using fresh material, generally still better results are achieved with respect to yield and purity of the valuable products.

The press cake can have a residual oil content, which can also be 20% or more. Despite such high residual oil contents, obtaining a protein phase with the invention is also achievable in a simple manner.

Step B:

If it is not present in comminuted form: comminuting the mixture of materials from step A) to disintegrate the hulls. If a press cake is used, this is disintegrated, ideally immediately after the pressing, still warm. In such a manner a comminuted material—a type of granules—is generated from the press cake. The mixture of materials that is (partially) deoiled in advance by a pressing operation is generally only comminuted, for example ground, or in any case hulls are disintegrated.

Step C:

The mixture of materials from step A) or B) that is provided and comminuted is dispersed with water. To one part of "comminuted product" are added preferably up to a maximum of 8, preferably up to a maximum of 5, parts of water. Then, water and comminuted product are stirred, in such a manner that a free-flowing pulp and/or a dispersion is yielded. The stirring proceeds preferably for more than 30 min, in particular for more than 1 h.

Step D

Next, the pH of the pulp (I) from step C) is adjusted to an alkaline range; preferably, the pH of the pulp or of the dispersion is adjusted with alkaline solution to pH 10 to 11. In the course of this the stirring is continued (carefully). The stirring time is preferably more than 30 min, preferably it is 1 h or more.

Step E

In this further step, at least one water-soluble organic solvent is added subsequently to adjusting the pH of the pulp in step D. Preferably, the dispersion, the pH of which has been adjusted to the alkaline range, is brought using the alcohol EtOH (preferably 30-60% strength) to an alcohol concentration of 20-15% or less, in particular 12% EtOH. In correspondence with the amount of water of the alcohol used, the amount of water in step C can be reduced by the water present in the alcohol, in particular in the 30-60% strength EtOH. Thereby, the hulls detach from the endosperm (cotyledon) with the residual oil and can be separated off, in particular by centrifugation.

Step F

In step F), therefore, a solid phase is separated off which comprises the hulls as the predominant fraction, preferably in a centrifuge in the centrifugal field from the pulp, or the pulp is clarified from hull solid fractions, in particular in a decanter.

This step is illustrated in FIG. 1 which shows a decanter 1 having a feed 2 wherein the hulls 3 are separated from the residual pulp 4.

The lighter phase of a centrifugal phase separation is hereinafter also occasionally termed top phase, and the solids phase the heavy phase. A middle phase would be situated accordingly inbetween with respect to the density thereof.

Figure 2:
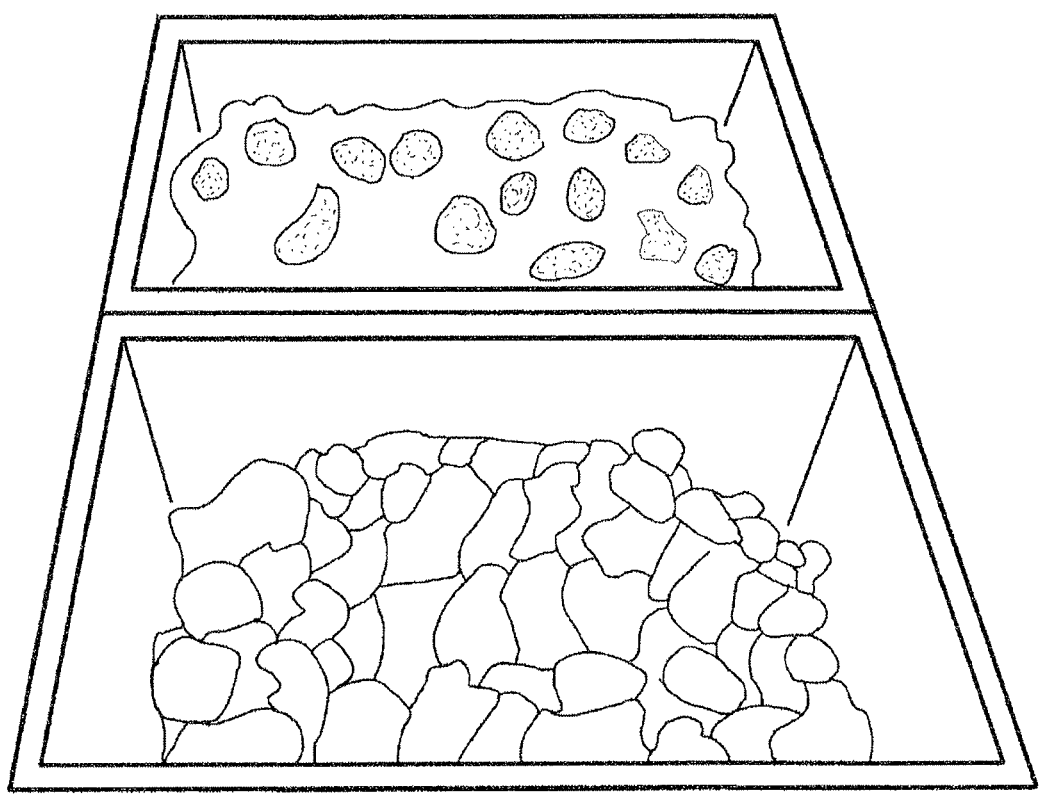
FIG. 2 shows schematically at the top a container of hulls from warm-pressed cake having white protein adhesions, and at the bottom hulls from cold-pressed cake without protein adhesions.

FIG. 2 shows purely schematically at the top a container of hulls from warm-pressed cake having white protein adhesions, and at the bottom hulls from cold-pressed cake without protein adhesions.

Step G

At all events very substantially hull-free pulp from step F) is then further processed. Preferably, the dissolved protein fraction from the hull-free pulp is precipitated, which protein fraction, together with the non-dissolved or solubilized protein part forms a fraction, the curd. The pH in this case is again further shifted into the acidic range, in particular to the pH range of pH=4.5 to pH=7.

Step H

Then the hull-free pulp, the pH of which has been shifted back into the acidic range is separated—preferably in a centrifuge, in particular in at least one decanter or in a separator—into valuable phases in one or two steps, of which one phase is a protein concentrate phase.

Particularly preferably, separation into the following two or three phases proceeds:

oily phase aqueous phase (polyphenol, carbohydrate and sinapic acid-containing)

protein concentrate phase (hereinafter also termed "protein curd")

or aqueous phase having an albumin content and residual oil content; and protein concentrate phase (protein curd);

The two-phase separation is then carried out when the raw material is relatively strongly deoiled and/or is present bound in the solids or if no intensive shearing effect for the liquid phase has been carried out in step 1. The addition of water or alcohol or alkaline solution or the like can also proceed in substeps. The oil as lighter phase contains triglycerides and is one of the valuable materials obtainable.

Preferably, the temperature during all of the method steps is below 60° C., in particular below 50° C., preferably between 40° C. and 50° C., as a result of which particularly valuable products may be obtained.

Denaturation of the proteins is a temperature- and time-dependent process. In addition, there is the condition in the alcoholic environment. The protein denaturation proceeds more rapidly the higher the temperature. In an aqueous environment, even in the case of actions of heat of 45-50° C., no irreversible protein denaturation is to be expected. However, this changes with the alcohol concentration. Even at ambient temperature, in the presence of highly concentrated alcohol, protein precipitation may be observed. The lower the alcohol concentration is now, the higher the temperature must be in order to denature the proteins. Or, vice versa: the more aqueous the alcohol concentration is, the higher the working temperature may be without the proteins being irreversibly damaged.

Therefore, a temperature as high as possible will be selected (for pure water), i.e. as far as possible reaching to 60° C., in order to bring as many materials as possible into solution, such as proteins, lecithins, glycolipids, etc. Thereby the cellulose, the lignin and salts such as Ca phytate can be separated off as insoluble components of the or with the hull fraction. However, it is necessary to ensure that the temperature remains sufficiently low in accordance with the process parameters of time and alcohol concentration (if necessary pressure).

The precipitated proteins are present as protein curd (heavy phase). They form one more of the valuable materials obtainable. This phase can readily be dried to a powder.

Overall, a protein concentrate phase that is also optically appealing and therefore readily further utilizable is obtained, which, in a color classification scale RAL, may be assigned the values RAL 1015 (light ivory) or RAL 1013 (oyster white). Standardized colors are designated as an RAL color (RAL GmbH, subsidiary of the RAL Institute). Each color is assigned a four-figure color number. In theory, any press cake can be used for the method.

The advantageous temperature statement for the method steps A to H does not relate to the pressing temperature in the generation of the press cake in oil generation. The higher the temperature was in the preceding process steps, the browner becomes the protein phase or curd fraction. This is due firstly to the Maillard reaction of sugars with proteins, and secondly to phenol oxidation. Compared with DE 10 2011 050 905 A1, in particular by the use of optimized selected starting material (preferably cold-pressed rape press cake, preferably very fresh), a particularly appealing, particularly readily further utilizable product is obtained.

The use of a cold-pressed material, in particular of a cold-pressed rape press cake (temperature during pressing advantageously below 70° C., particularly preferably even below 60° C.), as starting material and/or as the mixture of materials provided is particularly advantageous. Warm-pressed material is exposed during pressing to markedly higher temperatures (up to above 100° C.). By using cold-pressed material as starting material for the method according to the invention, a protein phase or "protein or curd phase" having markedly better properties (in particular with respect to the color markedly brighter and therefore more easily processable) and with a markedly higher yield can be obtained than when using warm- or hot-pressed starting material. This has not been previously recognized in the prior art. This is because customary rape press methods are targeted towards a high oil yield, for which reason, during pressing, relatively high temperatures are readily used. As a side effect, it must be stated that sinapine (a polyphenol) is degraded, which in itself would be advantageous for the protein fraction. In the method according to the invention, the original, that is to say unreduced, sinapine content in the cold-pressed cake, however, is nevertheless not a problem for the end product, since the polyphenolic compounds are substantially not found in the curd phase, since they transfer to the water phase.

Thus, the curd phase which, according to the method according to the invention, have been obtained from a press cake additionally deoiled with hexane in advance, was rather to be assigned the RAL color 1024 ochre yellow or 1014 ivory. The processing preferably proceeds under ambient pressure.

In the water phase, also, valuable components are still present, in particular it has a relatively high albumin content. To this extent, a filtration of the water phase from S8 for albumin concentration is rational and advantageous, in order in this manner to obtain the albumin phase as a further valuable material.

A particularly advantageous method variant may be illustrated with reference to the following example. In this case, the operations pass through a plurality of steps "S":

S1. Starting material is in this example pressed rape cake or (also sunflower seed meal or soybean meal), ideally pressed under mild and cold conditions, with typical residual oil contents of 20%; higher contents are also not a problem S2. The cake is disintegrated, ideally immediately after pressing, still warm.

S3. The cake granules are dispersed with water (one part cake and a maximum of six parts water) and carefully stirred (1 h)

S4. This dispersion is to be adjusted to pH 10 to 11 using alkaline solution and carefully stirred, usually for 1 h.

S5. The dispersion of 4 is to be brought to 12% EtOH concentration using EtOH (preferably 30-60% strength), thereby the amount of water in point 3 is reduced by the water present in this 30-60% strength EtOH.

S6. The hulls are thereby detached from the endosperm (cotyledon) with the residual oil and can be separated off by centrifugation.

S7. Precipitation of the protein by acidification to preferably pH=4.5 to 7.2 from the top phase (top phase: light phase of the separation of step S6 having a pH of preferably 9.7 to 10.5) for the separation: oil—aqueous phase—protein concentrate phase (protein curd) or separation into oil/water phase and protein concentrate phase; this step can be supported by an intensive shearing, in order to facilitate the oil release.

S8. Separating off the precipitated proteins as curd (heavy phase (generally solids phase or here curd phase)) and optionally triglycerides (as light oil) from the top phase (light phase), in particular by centrifugation.

S9. Filtration of the water phase from S8 for albumin concentration.

As an optional step 10, here the repeated washing of the curd with light EtOH-water may be mentioned=purity increase.

The wet separation of the hulls from the dissolved and swollen proteins with, taking place in parallel, displacement extraction of the triglycerides (oil phase) from oil- or residual oil-containing press cake or legume flour and parallel-proceeding polyphenol extraction is also particularly advantageous.

Advantages of the method according to the invention are:

1. Low dilutions: therefore low volumetric flow rates in the process,

2. Higher polyphenol concentrations during the extraction in the aqueous phase (method steps 2 to 5), 3. Native proteins in the end product, since the process is implemented at a maximum of 50-55° C. or below, 4. High protein yields with up to 45% (up to 70%) in the "curd phase" plus approximately 22-24% in the albumin phase, 5. Higher value end product because hulls and polyphenol, carbohydrate, phytic acid or phytates, lignin and cellulose are completely removed or depleted, contains "native" protein, the swellable fraction of which remains swellable, the fraction detachable under aqueous conditions remains water-soluble, virtually triglyceride-free (oil-), low residual oil values (principally polar lipids), 6. Unfavorable environment for microorganism growth owing to the slight alcohol concentration simplifies process hygiene, and 7. The alcohol can be circulated in dilute form.

Re Steps S1-S2

Instead of extracting unwanted materials from the highly deoiled, very finely comminuted starting material rape meal or rape cake—as is customary in the familiar methods—here, first the hulls are separated off in the wet state. This is achieved in a multistage process by first disintegrating the cake, without further comminuting the seed fragments.

In particular, it is of importance to leave the hulls as large as possible. Preferably, they should have a median diameter of 0.5 mm or more. Oil droplets do not need to be larger, of importance are not individual molecules or small molecular associations, but rather "particles".

Then, water is added in and in alkaline situations, the mixture is carefully stirred. The water-soluble part of the proteins is detached thereby, another part swells. The addition of aqueous alcohol displaces the free triglycerides from the dispersion as a specifically light phase. The lecithins, in particular phosphatidylcholine, are soluble at low alcohol concentrations (see EP 1272048 B1 and associated patent family).

In this combination alkaline solution—aqueous alcohol, there are two or three phases 1) Heavy=hulls and 2) light=protein-lecithin-polyphenol-carbohydrate together with oily foam; or 1) Heavy=hulls, 2) center=protein-lecithin-polyphenol-carbohydrate 3) light=triglyceride, preferably separable, in this manner preferably by centrifugation in the experiment in the glass beaker or on an industrial scale.

The more successful is separating off the hulls, the lower are the protein losses, and the purer is the end product. Even the hull swollen up to seven fold by water addition is heavier than the proteins in the alcohol-aqueous dispersion. This is essential for separation by gravity. However, the separation is made harder by a solid adhesion of the protein-containing aleurone bodies (honeycomb layer) to the hulls. These cells are thick-walled. Since the cell membrane of virtually all cells contains lecithins (in addition to proteins etc.), then, by suitable measures, the adhesion can be minimized by the lecithins being "brought into solution".

Specifically, this is achieved in that the aqueous phase has an alcohol concentration of 5-40% (see steps S2-S4), ideally 12% to 20%.

The quality of the starting material is especially important therefor. Usually, in the case of cold-pressed cake, the residual oil content is higher. This does not interfere in the method presented here. On the contrary: the gentle pressing is extremely helpful, the more moderate is the pressing temperature and the lower is the pressing pressure, the easier the subsequent separation of hulls and cotyledon (germ layers, the seed interior).

The method can also be applied to "customary", i.e. hot-pressed, press cake, except in this case the yields of proteins are correspondingly lower.

Re Steps S2 to S4) Dispersion Production

Producing the dispersion with water-aqueous alkali and alcohol has two purposes: firstly, the detachment from the hull, secondly, the extraction of phenolic compounds such as sinapine from the raw material. In this case, the wetting with fluid is important. However, shearing in the case of the dispersion formulation in steps 2-5 generated very small particles which led to the contaminants in the separated phases. Without a shear head mixer application, or without using a sawtooth disk mixer for steps 2-5, the protein content in the protein phase (after step 7 and drying) was: >60% with fresh material.

Using a shear head mixer or using a Frisam shear mixer, the protein content in the protein phase (after step 7 and drying) was: approximately 50% with old material.

Another test was carried out using hot-pressed expeller cake. The amount of hulls separable off in the first stage is reduced by the shearing from 20% to 16% and at the same time the amount of precipitatable protein from the clear phase increases from 38% to 42%. Purity remains relatively constant and low at 39-40%.

T=50° C., 30 min reaction time (re step S5) alcohol environment

In addition to the solution of the lecithins in the aqueous-alcoholic state, for improved separation of hulls, firstly, and triglycerides, secondly, separating off material in the slightly alcoholic state additionally has the advantage that growth of microorganisms in the process is made more difficult. This is a marked advantage in comparison with the purely aqueous methods and facilitates cleaning in place.

Re Step S6) Separation

In FIG. 1, "cold=cold-pressed cake; warm=warm-pressed cake; hot=conditioned and hot-pressed cake" example:

B1) Cold-pressed cake: 17% heavy phase as hull fraction from the feed with 20% of the cake proteins and 83% top phase as protein-polyphenol-oil-phosphatide-phase having 80% of the cake proteins 2) Warm-pressed cake: 26% heavy phase as hull fraction from the feed with 30% of the cake proteins and 74% top phase as protein-polyphenol-oil-phosphatide-phase having 70% of the cake proteins B3) Hot-pressed cake: 30% heavy phase as hull fraction from the feed with 50% of the cake proteins and 70% top phase as protein-polyphenol-oil-phosphatide-phase having 50% of the cake proteins.

Re Step S7) Protein Precipitation

From the top phase (top phase=light phase) of the separation in step S6, the proteins are precipitated by pH shift to the range of 4.5 to approximately 7. The water-insoluble proteins (swellable proteins) form, together with precipitated globulins, the protein fraction of the "protein curd". The liquid in this fraction has the same composition as the liquid of the middle phase (top phase without triglycerides). Since, however, the curd phase only makes up 10-30% of the feed, (containing 15-25% dry matter), quantitatively, also substantially fewer polyphenols may be found in the curd phase than in the middle phase, even though the concentration of the polyphenols, based on the water, is the same.

A protein phase of water-insoluble, but swollen proteins with globulins is thereby available which is depleted in polyphenol. This combination of alkaline-ethanolic environments in steps S2-S5, followed by an acid-alcohol environment for protein precipitation, represents very good conditions for a polyphenol extraction. Surprisingly, for rapeseed (sinapine and derivatives), here the observation for other polyphenols (tyrosol and derivatives, inter alia), from other fields, such as the processing of olives, has been confirmed, although markedly more reactive materials such as proteins and sugars are present in the suspension.

Dilutions as described in the literature thereby become obsolete, in order to arrive at equivalent polyphenol extraction rates as the aqueous systems (for instance as in again Kroll et al., "Rapssamenproteine—Struktur, Eigenschaften, Gewinnung and Modifizierung" [Rapeseed proteins—structure, properties, production and modification], Deutsche Lebensmittel-Rundschau, issue 3, 2007, p. 109).

Since the pure triglyceride is displaced from the liquid as a light phase, the residual oil content in the protein end product can be reduced to below 15%, also below 13%, based on dry matter.

Since the temperatures during the entire process can be <50° C., it is also possible to speak of a native end product.

Shearing the pulp to be further processed before the phase of separation of step H (before separating off the oil) and after step F) or G) is advantageous for improving the displacement extraction. This shearing can be carried out using a shearing device such as a homogenizer or an intensive mixer, in order in this manner to obtain still more oil.

Figure 3:
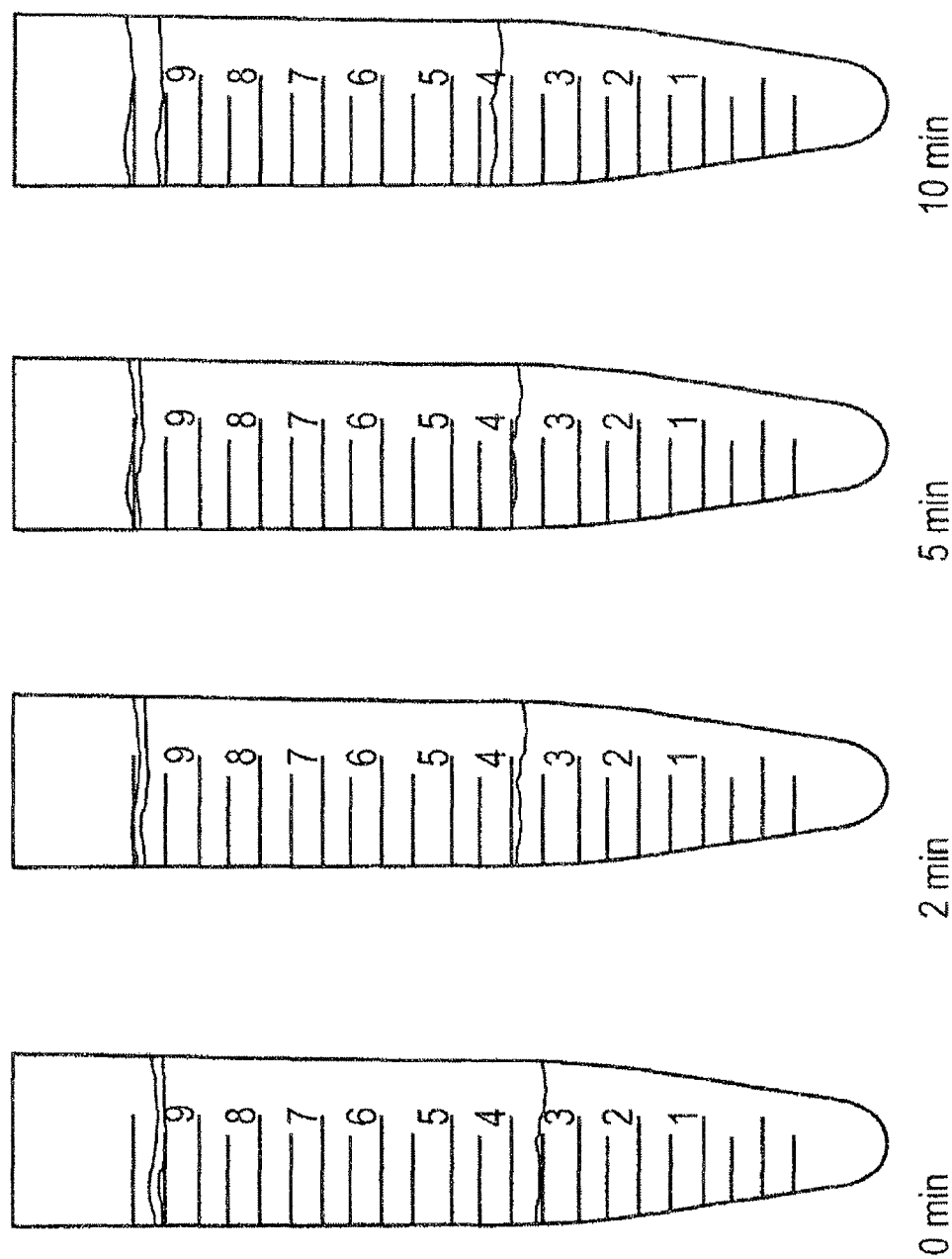
FIG. 3 shows schematic views of glass beakers containing samples.

FIG. 3 shows samples in which shearing was carried out for different times (0 min, 2 min, 5 min, 10 min). It may be seen that more oil is released in the right-hand picture (top rings in the sample glass). High pressures are generated locally by the shearing process.

Shearing using a shearing device can be carried out in the continuous process. Overall, preferably a continuous process is effected.

S8: Separation of the proteins as curd by means of a decanter or separator.

To increase purity, the protein curd can be washed. The curd can then be dried to a powder.

S9: Subsequently, advantageously, albumin extraction can proceed.

Figure 4A:
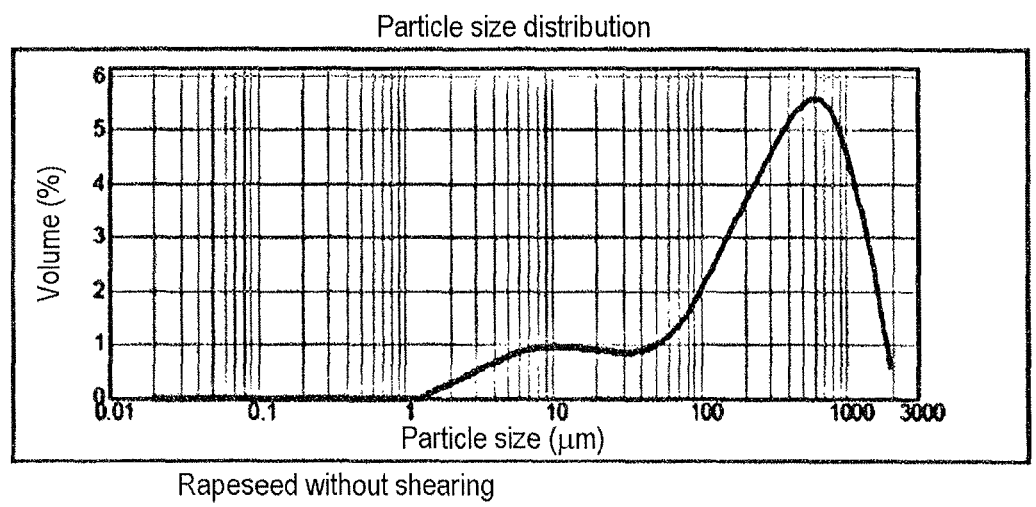
FIG. 4a, b show diagrams which illustrate the effect of shearing on the comminution of the hulls.
Figure 4B:
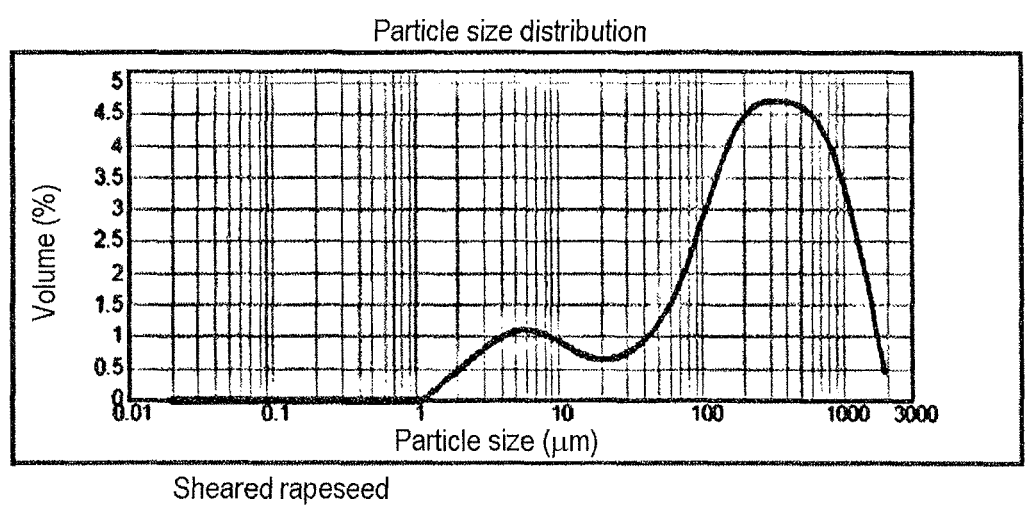

In summary, an advantageous method for obtaining proteins from native mixtures of materials is also provided, having the following steps: A) providing a native mixture of materials from seeds having hard fragmentable hulls, B) comminuting the mixture of materials, in order at all events to disintegrate the hulls without dispersing them too finely (preferably, the size of the comminuted hull fractions in a granulometric distribution in the manner of FIG. 4 should be between 100 and 2000 µm, in particular having a maximum between 300 µm and 900 µm, in particular around 600 µm, in each case at a relative frequency of more than 5%); C) dispersing the comminuted mixture of materials from step A) or B) with water; D) adjusting the pH of the pulp (I) from step C) to an alkaline range pH>9.5; E) adding the water-soluble organic solvent alcohol to the pulp of step C) subsequently to adjusting the pH of the pulp in step D; F) separating off a solids phase which comprises the predominant fraction of the hulls, preferably in a centrifuge in the centrifugal field; G) shifting the pH of pulp from step F) that is freed from hulls into the pH range of pH=4.5 to pH=7.2, and H) separating the hull-free pulp, the pH of which has been shifted back into the acidic range—preferably in a centrifuge, in particular in at least one decanter—in one or more steps into the following three valuable material phases: oily phase having a triglycerol content; aqueous phase having an albumin content and protein concentrate phase (protein curd).

It is further advantageous if the curd phase is dried. Here is advantageous to vaporize off from the quark any alcohol still present, preferably under vacuum, in order to keep the temperature low, and then dry the alcohol-free, aqueous curd to a powder. For this purpose a dryer-pulverizer, for example, is suitable. In this manner a storage-stable, readily handlable and also transportable product is provided.

The beneficial properties can be illustrated with reference to a protein phase obtained in the experiment:

Experiment 1 (for steps A-F): experimental batch: 95 kg of municipal water+23 kg of rapeseed (warm pressing) charged into a stirred tank and heated to 40° C. (steps A and C). Then, this product/water mixture is circulated by means of a monopump and a Fristam mixer at 1000 l/h for approximately 8 min (pH=6.2). Then, 4.1 l of 10% strength NaOH is added to pH=10 (step D). Then, the mixture is circulated without a Fristam mixer for 15 min at 1000 l/h and stirred. Then, 14.2 kg of ethanol (step E in one or more substeps) is added by means of a peristaltic pump directly into the circuit of the monopump. Residence time: 10 min. After approximately 50 min residence time, a further 2 kg of ethanol in 11 kg of water is mixed and added into a stirred tank. 10 min residence time. This suspension is separated by centrifugation (step F). In this case the yield is: 96.5 kg clear phase, 34 kg of solids. The hulls may be separated off readily.

Experiment 2: (A-F) experimental batch: 116 kg of municipal water+26 kg of rapeseed (cold pressing) charged into a stirred tank and heated to 40° C. Then, the mixture is circulated by means of a monopump and Fristam mixer at 1000 l/h for approximately 8 min (pH=5.8). 4.5 l of 10% strength NaOH are added to pH=10. Then the mixture is circulated without a Fristam mixer at 1000 l/h for 15 min. 17.2 kg of ethanol are added by means of a peristaltic pump directly into the circuit of the monopump. 10 min residence time. Thereafter, the mixture is separated in order to separate off the hull fraction. The yield is yield: 129.6 kg of clear phase, 26.5 kg of solids. The hulls may be separated off more easily thereby.

Experiment 3: (steps G and H for experiment 1): 96.5 kg of clear phase of experiment I (pH initially: 9.6) were shifted to pH 5 by means of 0.8 l of 25% strength hydrochloric acid, here advantageously at 45° C. (step G). This pulp can then be centrifuged, wherein a protein phase is obtained as heavy phase or solids phase (step H). Yield of clear phase: 64.3 kg. Yield of solids phase (curd-like) 9 kg.

Experiment 4 (steps G and H for experiment 2): 129.6 kg of clear phase of experiment II (pH initially: 9.5) were shifted to pH 5 by means of 1.2 l of 25% strength hydrochloric acid at 45° C. (step G). This pulp can then be centrifuged, wherein a protein phase is obtained as heavy phase or solids phase (step H). Yield: 83 kg of clear phase, 29.5 kg of solids (protein phase). Here, the yield of solids phase is particularly high.

A powder obtained in the manner of the abovementioned experiments and then obtained from dried curd typically has dry matter contents of 5-9%; in one sample produced from conventional press cake, 5.35%. The protein content is approximately 60%. The water binding capacity was determined at 1.8+/−0.2 ml of $H_2O$ per 1 g of dry matter of the protein powder, the oil-binding capacity at 0.49 to 0.63 g of oil/g of dry matter, and also the emulsifiability at 700 to 780 ml of oil/g of dry matter of the protein powder. Typical values for the protein solubility value NSI are 9 to 16%. The best results are achieved with the cold-pressed press cake.

In further experiments, it was surprisingly found that the stirring technique in the method is also of importance, which relates in particular to the stirring of step C) (and possibly D) and E)).

Thus, cold-pressed rapeseed press cake was processed in the procedure. In this case, in step C), the stirring is performed once with a blade stirrer and once with a propeller stirrer.

The blade stirrer should be operated in such a manner that it generates as little shear forces as possible during stirring, but a substantially uniformly laminar flow.

In the case of the propeller stirrer in the meaning of this application, stirring elements are also connected outside the axis of rotation, and thus via a disk or a ring or in the vicinity thereof, elements are present such as an open bell over the propeller elements. They therefore generate a relatively turbulent flow during stirring and exert higher shear forces on the product.

Blade stirrers are therefore those which generate substantially a laminar flow during stirring, which have relatively long blades and which are operated at a low speed of rotation. A ring or a disk or the like on the outer periphery of the blades or in the vicinity thereof (in the manner of an open cage or an open bell around the blades) is generally not present. Typical speeds of rotation are 0-100, also up to 150 rpm. In contrast thereto, the propeller stirrer, the blade diameter of which is somewhat small and the rotor speed of rotation somewhat high at up to approximately 700-800 rpm, generates high turbulence, for which reason the suspension is more strongly sheared.

In the further experiments, after the steps D) and E)—preferably with further stirring using the blade stirrer or the propeller stirrer—the hull-containing solids phase was separated off according to step F).

The liquid phase after separating off the hulls from a suspension of rapeseed press cake which contains 13.4% oil, 31.4% protein and 55.2% other matter (such as cellulose, phytic acid, polyphenols, saccharides, etc.) was, when the blade stirrer was used for stirring in step C) and possibly D) and E), markedly protein-richer than when a propeller stirrer was used. Approximately 75% of the proteins of the cake were found in the top phase, the dry matter of which comprised 52.3% protein, 13.0% oil and approximately 34% other matter. In contrast, only 62.5% of the proteins of the cake were found in the comparable top phase when a propeller stirrer was used. For this case, the top phase dry matter had only approximately 37% protein, approximately 14.7% oil, and also 48.0 other components.

Also visually, surprisingly, marked differences were found. The hull fraction of the centrifuge sample from the suspension when the blade stirrer was used appeared markedly more marbled. In this case, only 42% of the dry matter was separated off as top phase, and when the propeller stirrer was used, the fraction of the dry matter that was separated off was 50%.

On the basis of the analyses of the phases, it can be concluded that using the propeller stirrer, unwanted "other matter" is released (the white layer over the hulls is markedly larger in the case of the propeller stirrer (it is suspected this may be starch), and accordingly the protein losses with the hull fraction slightly increased (blade 30%, propeller 33%).

Furthermore, further advantageous method variants were able to be found.

Thus, a high alcohol, in particular ethanol, concentration causes a high oil content in the "globulin curd". It is particularly advantageous, in step E), therefore, when the alcohol concentration is less than 20%, in particular is 13-18%, particularly preferably 15%.

Too long a reaction time of pH 10 (overnight) likewise causes high oil contents in the globulin curd. Somewhat lower temperatures, in particular below 43° C., act advantageously in the globulin precipitation and separation and give rise to higher protein contents in the curd (column K, lines 34 and 35).

Furthermore, one or more of the following further measures appear as particularly advantageous: use of fresh material during pressing of the oil; cold pressing of the oil; gentle stirring with a blade stirrer (in step C), in this case the material should be sheared or even ground as little as possible; an alcohol content, in particular ethanol content of less than 20% appears particularly advantageous, since otherwise a higher oil content results in the curd.

The invention claimed is:
1. A method for obtaining proteins from native mixtures of materials, comprising the steps of:
   A): providing a native mixture of materials from seeds having hard fragmentable hulls;
   B): comminuting the mixture of materials, wherein the hulls are disintegrated;
   C): dispersing the comminuted mixture of materials with water, wherein per one part of comminuted mixture of materials, up to a maximum of 8 parts of water are added, and wherein the water and the comminuted mixture of materials are stirred such that a free-flowing pulp is yielded;
   D): adjusting a pH of the pulp of step C) to an alkaline range pH>9.5;
   E): adding a water-soluble organic solvent alcohol to the pulp subsequently to adjusting the pH in step D) such that an alcohol concentration of the pulp is less than 30%;

F): separating off a solids phase from the pulp, which has a predominant fraction of the hulls, to form a hull-free pulp;

G): shifting the pH of the hull-free pulp from step F) to a pH range of pH=4.5 to pH=7.2; and H): separating the hull-free pulp of step G) into a plurality of phases, wherein one of the plurality of phases is a protein concentrate phase.

2. The method as claimed in claim 1, wherein, in step H), the plurality of phases include:
an oily phase having a triglycerol content; and
an aqueous phase having an albumin content.

3. The method as claimed in claim 1, wherein, in step H), the plurality of phases include an aqueous phase having an albumin content and residual oil content.

4. The method as claimed in claim 2, wherein the aqueous phase is filtered.

5. The method as claimed in claim 1, wherein the protein concentrate phase has a value of RAL 1015 or RAL 1013 in a RAL color classification scale.

6. The method as claimed in claim 1, wherein after step A) no more than 31 days pass prior to step B).

7. The method as claimed in claim 6, wherein after step A) no more than 3 days pass prior to step B).

8. The method as claimed in claim 7, wherein, after step A) less than 12 hours or less than 1 hour pass prior to step B).

9. The method as claimed in claim 1, wherein, as the mixture of materials in step A), a cold-pressed material is used which was pressed at a temperature below 70° C.

10. The method as claimed in claim 1, wherein, in step C), the stirring proceeds for more than 30 minutes.

11. The method as claimed in claim 1, wherein the separating steps are each performed in a three-phase decanter, or in at least two steps in two-phase decanters.

12. The method as claimed in claim 1, wherein the water-soluble organic solvent alcohol is a linear aliphatic alcohol.

13. The method as claimed in claim 1, wherein a content of water-soluble organic solvent alcohol in the pulp after addition of the water-soluble organic solvent alcohol in step E) is less than 45% by volume.

14. The method as claimed in claim 1, wherein, before step H), the hull-free pulp is sheared.

15. The method as claimed in claim 1, wherein, before step H) and after step F) or G), the hull-free pulp is sheared.

16. The method as claimed in claim 1, wherein a temperature during steps A) through H) is below 60° C.

17. The method as claimed in claim 1, wherein a temperature in step H) is between 20 and 30° C.

18. The method as claimed in claim 1, wherein a temperature during steps A) through H) is below 50° C.

19. The method as claimed in claim 1, wherein a temperature during steps A) through H) is between 40° C. and 50° C.

20. The method as claimed in claim 1, wherein the protein concentrate phase is dried to form a powder.

21. The method as claimed in claim 1, wherein, in one or more of the steps C) and D) and E), stirring is performed using a stirrer such that a substantially laminar flow is generated in the stirring.

22. The method as claimed in claim 1, wherein, in one or more of the steps C) and D) and E), stirring is performed using a stirrer such that no product-damaging shearing action is generated during the stirring.

23. The method as claimed in claim 1, wherein, in step E), the adding of the water-soluble organic solvent alcohol to the pulp from step D) is performed subsequently to step D) such that the alcohol concentration of the pulp is between 10% and 20%.

24. The method as claimed in claim 1, wherein, in step E), the adding of the water-soluble organic solvent alcohol to the pulp from step D) is performed subsequently to step D) such that the alcohol concentration of the pulp is between 13% and 18%.

* * * * *